United States Patent
Barciszewski et al.

(10) Patent No.: US 7,923,578 B2
(45) Date of Patent: Apr. 12, 2011

(54) METHOD OF MANUFACTURING 3-(4-HYDROXYPHENYL)PROPANOIC ACID AMIDE, ITS APPLICATION IN THE MANUFACTURE OF ANTI-AGING COMPOSITIONS AND ANTI-AGING COMPOSITION

(75) Inventors: Jan Barciszewski, Poznan (PL); Leszek Rychlewski, Poznan (PL); Lech Celewicz, Poznan (PL); Krzysztof Ciszewski, Poznan (PL); Eliza Wyszko, Poznan (PL); Katarzyna Rolle, Gadki (PL)

(73) Assignee: Instytut Chemii Bioorganicznej Pan, Poznan (PL)

( * ) Notice: Subject to any disclaimer, the term of this patent is extended or adjusted under 35 U.S.C. 154(b) by 352 days.

(21) Appl. No.: 12/090,768

(22) PCT Filed: Oct. 18, 2006

(86) PCT No.: PCT/PL2006/000069
§ 371 (c)(1),
(2), (4) Date: Apr. 18, 2008

(87) PCT Pub. No.: WO2007/046721
PCT Pub. Date: Apr. 26, 2007

(65) Prior Publication Data
US 2008/0249334 A1    Oct. 9, 2008

(30) Foreign Application Priority Data

Oct. 20, 2005    (PL) .......................................... 377747

(51) Int. Cl.
C07C 233/05    (2006.01)
C07C 231/02    (2006.01)

(52) U.S. Cl. ........................................ 564/170; 564/139
(58) Field of Classification Search ................... 564/139, 564/170
See application file for complete search history.

(56) References Cited

FOREIGN PATENT DOCUMENTS

| | | |
|---|---|---|
| DE | 233551 | 4/1911 |
| EP | 1559422 A1 | 8/2005 |
| WO | 2005062851 A2 | 7/2005 |

OTHER PUBLICATIONS

Bebbington et al, J. Med. Chem, 2000, 43, 2779-2782.*

* cited by examiner

*Primary Examiner* — Shailendra Kumar
(74) *Attorney, Agent, or Firm* — Joe A. Powell; Christopher L. Parmelee; Walker & Jocke (57) ABSTRACT

The subjects of the present invention are a method of manufacturing 3-(4-hydroxyphenyl)propanoic acid amide, its application in the manufacture of anti-aging compositions and an anti-aging composition. As phloretamide possesses a series of biological properties it might be use as a composition for skin having excellent anti-aging effect to prevent the sagging of skin and loss of luster.

12 Claims, 12 Drawing Sheets

Fig. 1

Control

JC-1 staining

Control

Lysosomal activity:

Control

Cytotoxicity in fibroblast cells (5 weeks)

METHOD OF MANUFACTURING 3-(4-HYDROXYPHENYL)PROPANOIC ACID AMIDE, ITS APPLICATION IN THE MANUFACTURE OF ANTI-AGING COMPOSITIONS AND ANTI-AGING COMPOSITION

This application is a 371 of PCT/PL2006/000069, filed Oct. 18, 2006.

The subjects of the present invention are a method of manufacturing 3-(4-hydroxyphenyl)propanoic acid amide (phloretamide), its application in the manufacture of anti-aging compositions and an anti-aging composition. As phloretamide possesses a series of biological properties it might be use as a composition for skin having excellent antiaging effect to prevent the sagging of skin and loss of luster.

3-(4-hydroxyphenyl)propanoic acid amide possesses a series of biological properties. Low-molecular mass compounds in plant juices play a very significant role in the growth and development of plant shoots. It was shown that the soft of *Malus domestica* (cv. Lobo) contains 3-(p-hydroxyphenyl)propanoic acid amide, also called phloretamide (No. CA 23838-70-2). It was identified with the aid of mass spectrometry and NMR spectroscopy. The important point is that secreted plant juice has a much higher concentration of phloretamide than internal plant juices [H. Rybicka *Phloretamid in fruitlets of apple tree (Malus domestica)*, www.app-online.pl, Acta Physiologiae Plantarum, vol. 18/1996, p. 359]. Structurally similar compounds, such as hydroxycinnaminic acids are some of the major phenolic compounds occurring in plants. In particular, p-hydroxycinnaminic acid is a common component occurring in higher plants [Bearder, J. R. *Plant hormonem and Rother growth substances-their backround, sructures and occorence*, Encycl. Plant Physiol., New ser., vol. 9, 9-112, Sringer Verlag, Berlin-Heidelberg-New York, 1980; Harbone J. B. *Plant phueolics*, Encycl. Plant Physiol., New ser., vol. 8, 329-402, Sringer Verlag, Berlin-Heidelberg-New York, 1980; Herrmann, K. *Hydroxyzimtsaeure und Hydroxybenzoesaeure enthaltende Natrstoffe in Pflanzen*, Fortschr. Chem. Org. Naturstoffe 35, 73-132 (1978)]. It was determined that secondary amides of hydroxycinnaminic acids prolifically occur in the fertile flowers of *Araceae*, whereas they were not found in sterilized flowers [Ponchet M., Martin-Tanguy J., Maras A., Martin C. *Hydroxycinnamoyl acid amidesand aromatic amines in the inflorescences of some Araceae spacies*, Phytochemistry 21, 2865-69, 1982.

Furthermore, the presence of dihydroxycinnaminic acids were found in certain plants [Harbone J. B. *Plant phenolics*, Encycl. Plant Physiol., New ser., vol. 8, 329-402, Sringer Verlag, Berlin-Heidelberg-New York, 1980; Herrmann, K. *Hydroxyzimtsaeure und Hydroxybenzoesaeure enthaltende Natrstoffe in Pflanzen*, Fortschr. Chem. Org. Naturstoffe 35, 73-132 (1978)]. Namely phloretic acid (dihydro-p-hydroxycyinnaminic acid, 3-[p-hydroxyphenyl]-propanoic acid) has been found in root tips. The presence of phloretamide in xylem fluid (wood tissue plant juice) which is shed under pressure by apple trees during flowering likely plays a significant role in their physiology. This is supported by the presence of secondary amides of hydroxycinnaminic acids in the reproductive tissues of plants [H. Rybicka 3-[p-hydroxyphenyl]-propionic acid amide (phloretamide) In root exudate of *Malus*, Biochem. Physiol. Pflanzen 179, 303-309, 1984].

Short-term studies are best suited to determine whether tested compounds have any immediate toxic effects or if they are mitogenic. From a skin aging point of view it is extremely important to rule out these possibilities. This is to say that for any chemical to be potentially useful as an anti-aging compound, it should neither kill the cells nor induce cell division in fibroblasts. Based on these results, selection can be made for testing the long-term anti-aging effects.

A method of obtaining 3-(4-hydroxyphenyl)propanoic acid amide is known. It is based on using a solution of ammonia in anhydrous methanol to treat ethyl ester of 3-(4-hydroxyphenyl)propanoic acid at a high temperature. That reaction takes place in an autoclave or a sealed glass pipe (at increased pressure).

Patent application EP1523469 (published Apr. 20, 2005) presents a method of obtaining amide derivatives of cinnaminic acid used as selective inhibitors of amine oxidase (MAO-B). Patent descriptions US2001039035 (published Nov. 8, 2001) and WO0028077 (published May 18, 2000) present a method of increased the efficiency of the conversion of phenolic derivatives to products using peroxidase. This method encompasses the following stages of a reaction of a conjugate containing a detectible, tagged phenol with peroxidase in the presence of a catalyst. This may be an inorganic salt, or an organic compound characterized by particular formulae, where X means B(OH)2, Y is I, or in which X represents OH, Y is a halogen, or Q-R in which Q is a linear or branched 1-12 heteroatomic alkyl, in which binding heteroatoms are C, N, O, or S, in which the bonds connecting the heteroatomic alkyl chain may optionally encompass a substitute selected from among —OH, —COOH, —NH2, and —SH, where R is additionally selected from among —OH, —COOH— and, —NH2, or —CH3; or a mixture of inorganic or organic salts. The descriptions additionally cover compounds where R1 constitutes —CH2OH, or —COOH, and n is 1-8.

Patent description CA2009009 (published Aug. 2, 1990) presents the pharmaceutical application of cinnaminic acid amide derivatives. In this solution, derivatives of these amides are characterized by formulae in which X is a halogen effective as a muscle relaxant.

Patent description CN1035034 (published Aug. 30, 1989) presents insect flight inhibitors. In these compounds, X<1> and X<5> are either hydrogen or a C1-4 alkyl, a halogen or a halogen-substituted C1-4 alkyl; X<2>, X<3> and X<4> are selected from among hydrogen and a C1-4 alkyl, hydroxy-groups, C1-4 alkoxy- and phenoxy-; R<1> and R<2> are either hydrogen or a C1-4 alkyl; R<3> and R<4> in which each is a hydrogen or which together form a double bond binding —CR<1>R<3>- and —CR<2>R<4>-; and Y constitutes a hydroxymethyl, -formyl, -cyano, or -carbamoyl group N-substituted with one or two identical or different C1-4 alkyl groups, -carboxy or carboxyl ester or carboxylate salt.

Patent description HU185312 (published Jan. 28, 1985) presents a process of eliminating protective aminoacid groups from peptides in a reaction with liquid metallic sodium.

Patent description JP57046915 (published Mar. 17, 1982) presents anti-allergic compounds containing cinnamide derivatives.

Patent description D2540552 (published Mar. 25, 1976) presents derivatives of cycloalkyl 1-aryloxy-3-amino-2-propanols.

Patent description DE2412032 (published Oct. 16, 1975) presents water-soluble diazide dyes.

Patent description IL47892 (published Apr. 30, 1978) presents cinnamide derivatives, their synthesis and pharmaceutical compositions which contain them. This solution describes cinnamide compounds characterized by formulae in which X is a chloride, bromide or iodide and R is a hydrogen or an alkyl of 1 to 3 carbons, where as a pharmaceutical composition it is useful in the treatment or prevention of convulsions.

Patent description GB923357 (published Apr. 10, 1963) presents cinnamide derivatives and their manufacture. This solution pertains to compounds in which R is an alkoxy substitute, and R1 and R2 are either hydrogen or an alkyl, in which the radical contains at most 6 carbon atoms, and n is 0, 1 or 2 or non-toxic salts of their acids. The solution also describes the method of their manufacture through the condensation of certain pirydyl or pirydyl-alkyl amines with acyl substituents of appropriately substituted cinnaminic acid, for example halogenated, estrified or with an anhydrate.

Despite the above described method of synthesis 3-(4-hydroxyphenyl)propanoic acid amide, there is still a need to obtain an optimal method of manufacturing this compound, while at the same time obtaining the highest possible process efficiency, with particular emphasis on its utility in the pharmaceutical and cosmetic industries.

The goal of the present invention is to proceed a method which may be used to manufacture 3-(4-hydroxyphenyl)-propanoic acid amide facilitating its further application in the cosmetic and pharmaceutical industries and the application of this compound as an anti-aging preparation, to obtain an external composition for skin having excellent antiaging effect to prevent the sagging of skin and loss of luster.

The embodiment of such a stated goal and the solution of problems described in the state of the art dealing with the synthesis of 3-(4-hydroxyphenyl)propanoic acid amide with the concurrent achievement of the highest possible process efficiency, such that the phlorethamide may be utilized in the manufacture of anti-aging compositions, have been achieved in the present invention.

The subject of the present invention is a method of manufacturing 3-(4-hydroxyphenyl)propanoic acid amide characterized that the synthesis of 3-(4-hydroxyphenyl)propanoic acid amide is performed using active 4-nitrophenyl ester where the concentration of 3-(4-hydroxyphenyl)propanoic acid is 0.12-0.0012 mol, where the reaction is performed with ammonia at room temperature, and the 4-nitrophenol in ethyl acetate is supplemented with N,N'-dicyclohexylocarbodiimide, then the reaction mixture is stirred, the N,N'-dicyclohexylurea precipitate is then filtered out and dried under vacuum, the remainder is supplemented with anhydrous methanol saturated with ammonia (10 cm$^3$) and the reaction mixture is stirred and evaporated until dry, then the remainder is loaded onto a silica gel chromatography column, and the latter is washed with chloroform-metanol (50:1, v/v), whence the chromatographically clean product is crystallized from methanol and then dried in a vacuum dessicator over phosphorus pentoxide yielding 3-(4-hydroxyphenyl)propanoic acid amide.

Preferentially, 0.5-5 g of 3-(4-hydroxyphenyl)propanoic acid solution are used, with 0.5-5 g 4-nitrophenol in ethyl oxide, 5-15 times excess N,N'-dicyclohexylcarbodiimide in relation to 4-nitrophenol, and the anhydrous methanol saturated with ammonia is between 5-30 cm$^3$, wherein the reaction mixture is mixed in a temperature range of 0-10° C. for 10-50 min, whereafter it is mixed at room temperature for 1.5-3 h, then the precipitated N,N'-dicyclohexylurea is filtered out and washed in 2-15 cm$^3$ ethyl acetate.

Figure 1:
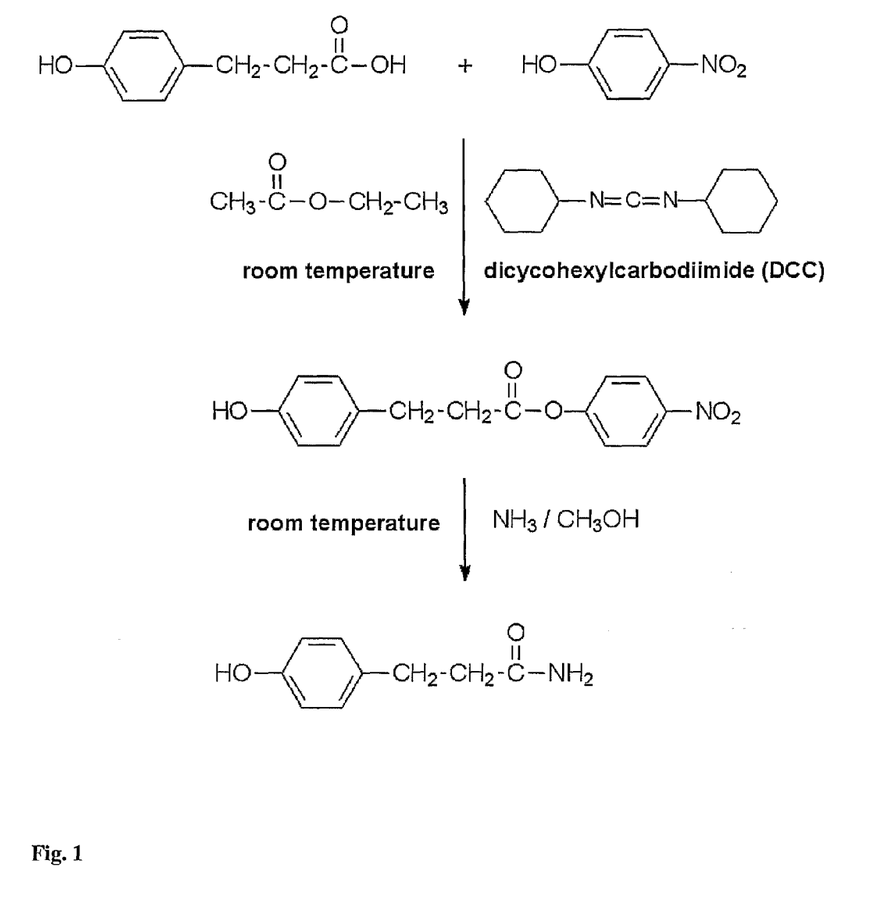
FIG. 1 presents the described synthesis of phloretamide.
Figure 2A:
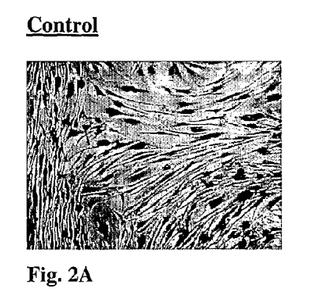
FIG. 2 represents the effects on the morphology of dermal fibroblasts (SNF25 p 23) after 11 days of phloretamide treatment (at 20× magnification).
Figure 2B:
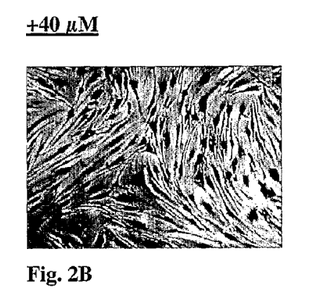
Figure 2C:
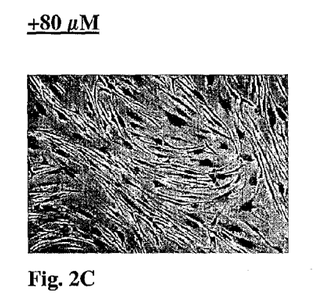
Figure 2D:
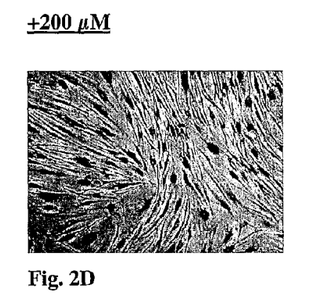
Figure 2E:
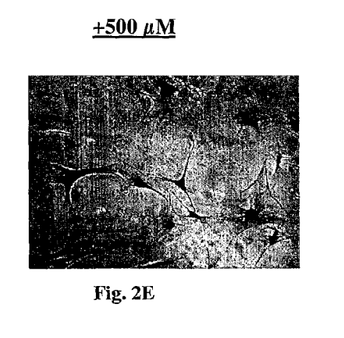

Preferentially, the method of manufacturing 3-(4-hydroxyphenyl)propanoic acid amide is that presented in FIG. 1.

The next subject of the present invention is the application of 3-(4-hydroxyphenyl)propanoic acid amide in the manufacture of anti-aging compositions. Preferentially, when in that in the manufacture of anti-aging compositions the synthesis of 3-(4-hydroxyphenyl)propanoic acid amide is performed using active 4-nitrophenyl ester where the concentration of 3-(4-hydroxyphenyl)propanoic acid is 0.12-0.0012 mol, where the reaction is performed with ammonia at room temperature, and the 4-nitrophenol in ethyl acetate is supplemented with N,N'-dicyclohexylocarbodiimide, then the reaction mixture is stirred, the N,N'-dicyclohexylurea precipitate is then filtered out and dried under vacuum, the remainder is supplemented with anhydrous methanol saturated with ammonia (10 cm$^3$) and the reaction mixture is stirred and evaporated until dry, then the remainder is loaded onto a silica gel chromatography column, and the latter is washed with chloroform-metanol (50:1, v/v), whence the chromatographically clean product is crystallized from methanol and then dried in a vacuum dessicator over phosphorus pentoxide yielding 3-(4-hydroxyphenyl)propanoic acid amide.

Preferentially, when in that in the manufacture of anti-aging compositions the synthesis of 3-(4-hydroxyphenyl)propanoic acid amide 0.5-5 g of 3-(4-hydroxyphenyl)propanoic acid solution are used, with 0.5-5 g 4-nitrophenol in ethyl oxide, 5-15 times excess N,N'-dicyclohexylcarbodiimide in relation to 4-nitrophenol, and the anhydrous methanol saturated with ammonia is between 5-30 cm$^3$, wherein the reaction mixture is mixed in a temperature range of 0-10° C. for 10-50 min, whereafter it is mixed at room temperature for 1.5-3 h, then the precipitated N,N'-dicyclohexylurea is filtered out and washed in 2-15 cm$^3$ ethyl acetate.

The next subject of the present invention is an anti-aging composition, characterized in that it contains 3-(4-hydroxyphenyl)propanoic acid amide at a concentration between 1 and 500 µmol.

Preferentially, the composition contains 3-(4-hydroxyphenyl)propanoic acid amide, obtained through the synthesis of 3-(4-hydroxyphenyl)propanoic acid amide is performed using active 4-nitrophenyl ester where the concentration of 3-4-hydroxyphenyl)propanoic acid is 0.12-0.0012 mol, where the reaction is performed with ammonia at room temperature, and the 4-nitrophenol in ethyl acetate is supplemented with N,N'-dicyclohexylocarbodiimide, then the reaction mixture is stirred, the N,N'-dicyclohexylurea precipitate is then filtered out and dried under vacuum, the remainder is supplemented with anhydrous methanol saturated with ammonia (10 cm$^3$) and the reaction mixture is stirred and evaporated until dry, then the remainder is loaded onto a silica gel chromatography column, and the latter is washed with chloroform-metanol (50:1, v/v), whence the chromatographically clean product is crystallized from methanol and then dried in a vacuum dessicator over phosphorus pentoxide yielding 3-(4-hydroxyphenyl)propanoic acid amide.

Preferentially, 0.5-5 g of 3-(4-hydroxyphenyl)propanoic acid solution are used, with 0.5-5 g 4-nitrophenol in ethyl oxide, 5-15 times excess N,N'-dicyclohexylcarbodiimide in relation to 4-nitrophenol, and the anhydrous methanol saturated with ammonia is between 5-30 cm$^3$, wherein the reaction mixture is mixed in a temperature range of 0-10° C. for 10-50 min, whereafter it is mixed at room temperature for 1.5-3 h, then the precipitated N,N'-dicyclohexylurea is filtered out and washed in 2-15 cm$^3$ ethyl acetate. Preferentially, the composition is applicable in the cosmetics and/or pharmaceutical industries.

BRIEF DESCRIPTION OF THE DRAWINGS

The attached figures facilitate a better explanation of the nature of the present invention.

FIG. 2: A, B, C, D and E were taken from a one step growth curve experiment after 11 days of treatment. At higher doses the cells appeared to be large in appearance, irregularly arranged and few in number. (FIG. 2E).

DETAILED DESCRIPTION

Below, there are example embodiments of the present invention defined above.

Example 1

Synthesis of 3-p-hydroxyphenyl-propionic acid amide

N,N'-dicyclohexylcarbodiimide (2.48 g, 0.012 mol) was added to chilled (0° C.) 3-(4-hydroxyphenyl)propanoic acid solution (2 g, 0.012 mol) and 4-nitrophenol (1.95 g, 0.014 mol) in ethyl acetate (25 $cm^3$) and mixed magnetically at 0° C. for 30 min. The reaction mixture was then stirred magnetically for 2 h at room temperature. Thereafter, the precipitated N,N'-dicyclohexylureaa was filtered out, washed using ethyl acetate (5 $cm^3$) and the combined filtrates were evaporated until dry. Anhydrous methanol saturated with ammonia (10 $cm^3$) was added and the reaction mixture was stirred magnetically for 2 hrs, thereafter the mixture was evaporated until dry, and the remainder was loaded onto a chromatography column packed with Merck 60H silica gel (5-40 μm). The column was eluted with chloroform-methanol (50:1, v/v). The chromatographically purified product was crystallized out of the methanol and then vacuum desiccated over phosphorus pentocide yielding 1.45 g 3-(4-hydroxyphenyl)propanoic acid amide (75% efficiency) (FIG. 1).

Example 2

Anti-Aging Applications

The aim of these experiments was to determine the effects of short-term treatment of human skin fibroblasts with novel "test compounds" on a variety of biological characteristics of human skin fibroblasts, in order to select for potential anti-aging properties.

The parameters studied were: cell attachment, survival, growth, mitochondrial activity, reversion studies, proteasomal-activity, lysosomal activity, and morphology of mid passage cultures of adult human skin fibroblasts. Additionally some pilot studies were performed with late passage near to senescence to test for "age reversal effects".

Test solution preparation: Stock solutions of 8 mM for the 3-p-hydroxyphenyl-propanoic acid amide were prepared by dissolving about 30 mg/ml in Hank's buffer to a final volume of 30 ml. In brief, the stock solutions were filter sterilized, stored at 4° C., and were used for experiments at their appropriate dilutions in cell culture media as required.

Cell culture: All experiments were performed on mid- and late passage cultures of normal human adult skin fibroblast line, designated Senetek SNF25 (40-75% life span completed). In order to check the effects of test compounds on senescent cells, late passage cells with about 75% lifespan completed were used. SNF25 cell line was established from a mammary skin biopsy obtained from a young, non-smoking and healthy female at the time of breast reduction operation. Normal culture conditions of medium (DMEM) containing antibiotics, 10% fetal calf serum, and incubation at 37° C., 5% $CO_2$ with 95% humidity were used. The effects of the test chemicals were determined in the following conditions:

Growth characteristics: Short-term growth experiments were performed using 24-well tissue culture plates (growth area 1.9 $cm^2$) and flat bottom 96 well plates (growth area 0.328 $cm^2$). Freshly prepared cell suspensions from mass cultures of SNF25 cells maintained in the lab were used. About 10,000 cells/well were seeded into 6 sets of 24-well plates. The cells were either allowed to attach and stabilize for 24 hours in normal culture medium or were directly added to the culture medium of a final concentration (range 40 μM to 500 μM). Culture medium was changed with the addition of test chemicals weekly. The numbers of cells were counted after different days of treatment in 2 wells from each concentration of the test chemical, by following the normal method of cell trypsinization and counting using a Coulter Counter. The third well in each category was fixed with cold methanol and stained with Giemsa stain for permanent record and for photography. The experiment was carried on until the cultures became fully confluent and no further growth was possible.

Cell survival, toxicity and JC-1 staining: Cell survival after exposure to various doses was measured with the 3-(4,5 dimethylthiazol-2-yl)-2,5-diphenyltetrazolium bromide (MTT) assay. About 5,000 cells were seeded per well in a 96-well plate for 24 hours before the experiment. Cells were then treated with various doses of the compound to be tested. The wells were washed in Hank's and new medium was added. After three days, MTT (Sigma, M2128) was added at 0.5 mg/ml in medium. After 4 h, MTT was removed and isopropanol and HCl were added to dissolve the MTT crystals for 12-16 h. The absorbance was measured at 595 nm.

Lysosomal activity: Neutral Red is preferentially taken up into the lysosomes of the cell. Fibroblast cells were maintained in culture and exposed to test compounds over a range of concentrations. The cultures were visually examined after 72 hours, and the number of viable cells and/or the total cell protein content determined, after 72 hours exposure, by the Neutral Red Uptake method. Individual wells of a 96-well tissue culture microtiter plate were inoculated with 0.2 ml of the appropriate media containing cells (usually 3×$10^3$ cells). After 1 day of incubation, the media were removed and replaced with unamended (control) medium or with medium amended with varied concentrations of the compound to be tested. After 3 days of exposure to the compound, media were removed and replaced with media containing 0.001% NR. The assay plate was then returned to the incubator for another 3 h to allow for uptake of the supravital dye into the lysosomes of viable cells. Thereafter, the media were removed and the cells were rapidly washed with 0.5% formaldehyde-1% $CaCl_2$ followed by 0.2 ml of a solution of 1% acetic acid-50% ethanol to extract the dye from the cells. After 10 min at room temperature and a brief but rapid agitation on a microtiter plate shaker, the plates were transferred to a microplate spectrophotometer equipped with a 540-nm filter to measure the absorbance of the extracted dye. The toxicities of the various compounds were compared with those of the control cultures by computing the data obtained.

Proteasomal activity: Chymotrypsin-like activity in cell extracts prepared from treated and untreated cells was determined by in vitro degradation of oligopeptides by the proteasome.

5-Bromo-2'-deoxy-uridine labelling and detection using Elisa plate reader: Toxicity studies are performed using the BrdU-assay, which is based on the measurement of the incorporation of 5-bromo-2-deaoxyuridine during DNA synthesis and a marker for cell proliferation. The proportion of cells undergoing DNA duplication, and thus entering the next round of cell division, was determined by labeling the cells with bromodeoxyuridine, using a commercially available kit (Roche Diagnostics GmbH). Briefly, cells were cultured in a micro titre 96 well plate. BrdU was added to the culture medium and was incorporated into freshly synthesized DNA (resulting conc.110 µM). Plate was then incubated for about 2-18 hrs and fixed with 200 µl ethanol fixative (0.5 µM ethanol/HCl) after washing with PBS. 100 µl of nuclease working solution (dilution 1:100 with incubation buffer) per well for 30 min at 37° C. in absence of $CO_2$, the nuclear treatment improves the accessibility of the BrdU by the antibody detection. 100 µl of anti-BrdU-POD, Fab fragments are added with 9.9 µl of PBS and BSA (final conc. 200 µg/ml), antibody conjugate is now removed and washed with PBS. The final step involves addition of 100 µl of peroxidase per well incubated at room temperature until positive samples showed a green colour, which was clearly distinguishable from the colour of pure peroxidase substrate. The absorbance was measured at 405 nm with reference at 490 nm and was directly correlated to the level of BrdU incorporated in the cell.

Results and comments

Figure 8:
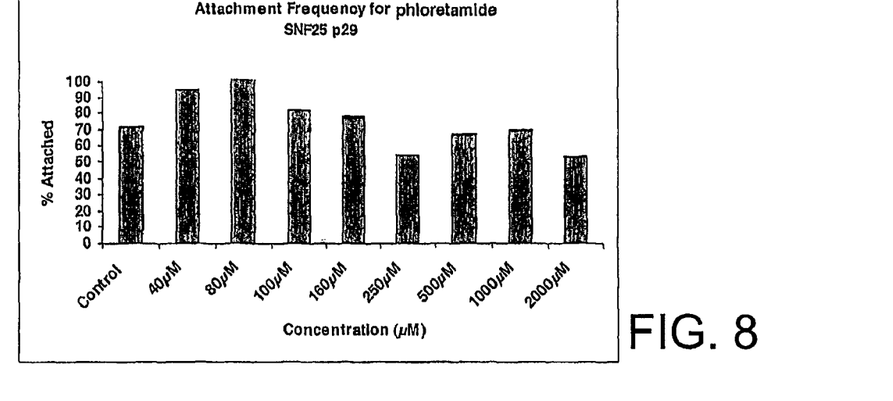
FIGS. 8-14 illustrate graphs associated with the present invention.

Cell attachment—As illustrated in FIG. 8, the percentage of cells attached to the surface of the culture flask was not affected to any significant extent after six hours of treatment with 40 11 M to 2 mM phloretamide.

Improved attachment was observed at 40 µM and 80 µM (20-30%). This compound is not immediately toxic to human dermal fibroblasts. Therefore, for all further experiments, phloretamide could be added to the culture medium at the time of seeding the cells.

Figure 9:
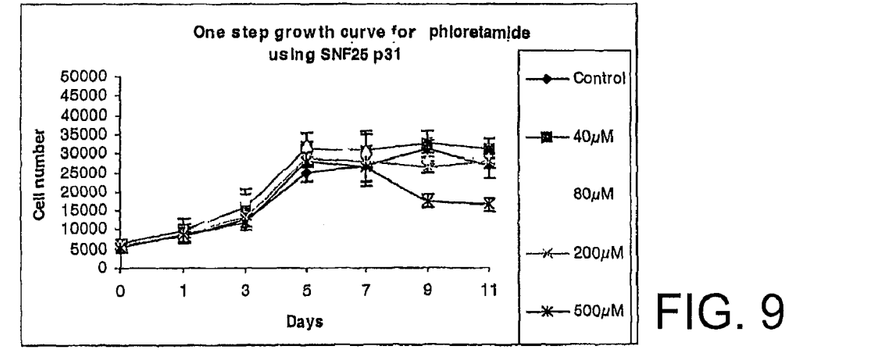

Short-term growth—The effects of phloretamide treatment on short-term growth are shown on graph in FIG. 9 and in FIG. 2.

Cell growth peaked at day 5 for almost all doses. After 11 days of treatment, 10-20% increase in cell numbers was observed in cells treated with 40 µM to 200 µM phloretamide. However, cellular growth was significantly inhibited by more than 50% at higher concentrations (500 µM). It shows that dose range between 40 µM-200 µM of phloretamide seems suitable for the long term treatment of human skin fibroblasts.

Effects on the morphology of dermal fibroblasts (SNF25 p 23) after 11 days of 3-p-hydroxyphenyl-propanoic acid amide treatment (at 20× magnification)-Pictures shown in FIG. 2: A, B, C, D and E were taken from a one step growth curve experiment after 11 days of treatment. Cytotoxicity of cells was seen at doses greater than 200 µM. At higher doses the cells appeared to be larger, irregularly arranged and sparse (FIG. 2 E).

Figure 10:
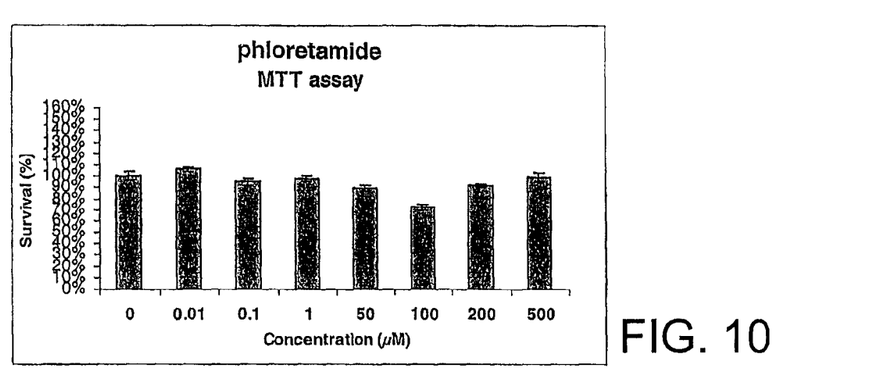

Mitochondrial activity—a wide range of doses (ranging from: 0, 01 µM-500 µM) on middle aged dermal fibroblasts tested for determining the mitochondrial effects on phloretamide is presented in FIG. 10.

3-p-hydroxyphenyl-propionic acid amide treatment has no negative effects on the activity of mitochondria in dermal fibroblasts until a dose of 500 µM. There shows to be no induction of cell growth within the tested range of doses.

Figure 3:
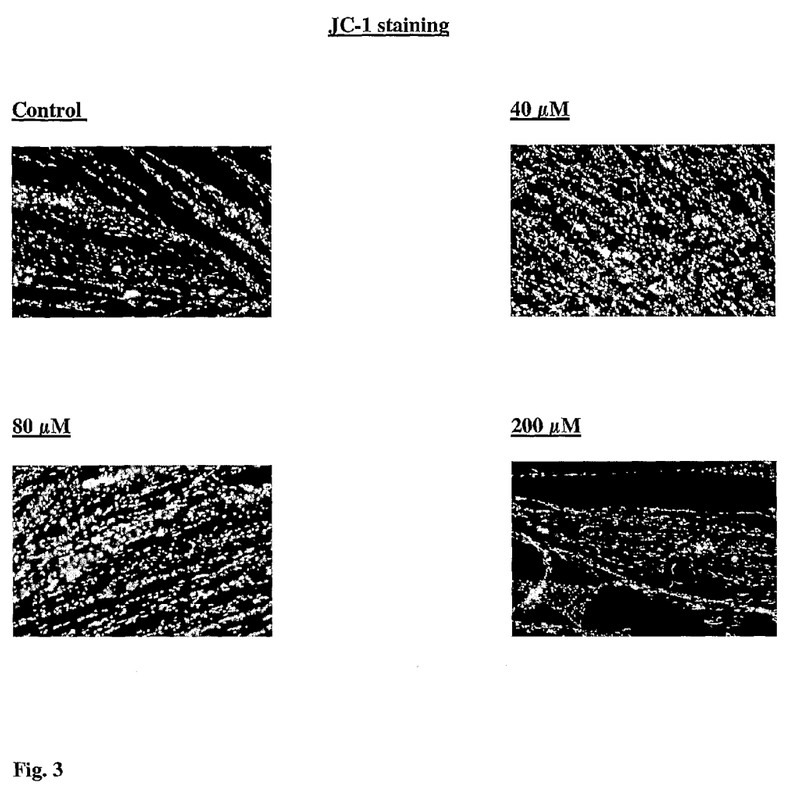
FIG. 3 presents the localization of JC-1 in SNF25 p44 cells using phloretamide by fluorescence microscopy. The population of cells shown in the FIG. 3 show polarized mitochondria from living cells marked by punctuate orange-red fluorescent staining by the formation and maintenance of J-aggregates.

Localization of JC-1 in SNF25 p 44 cells using phloretamide by fluorescence microscopy is shown on FIG. 3.

Figure 4:
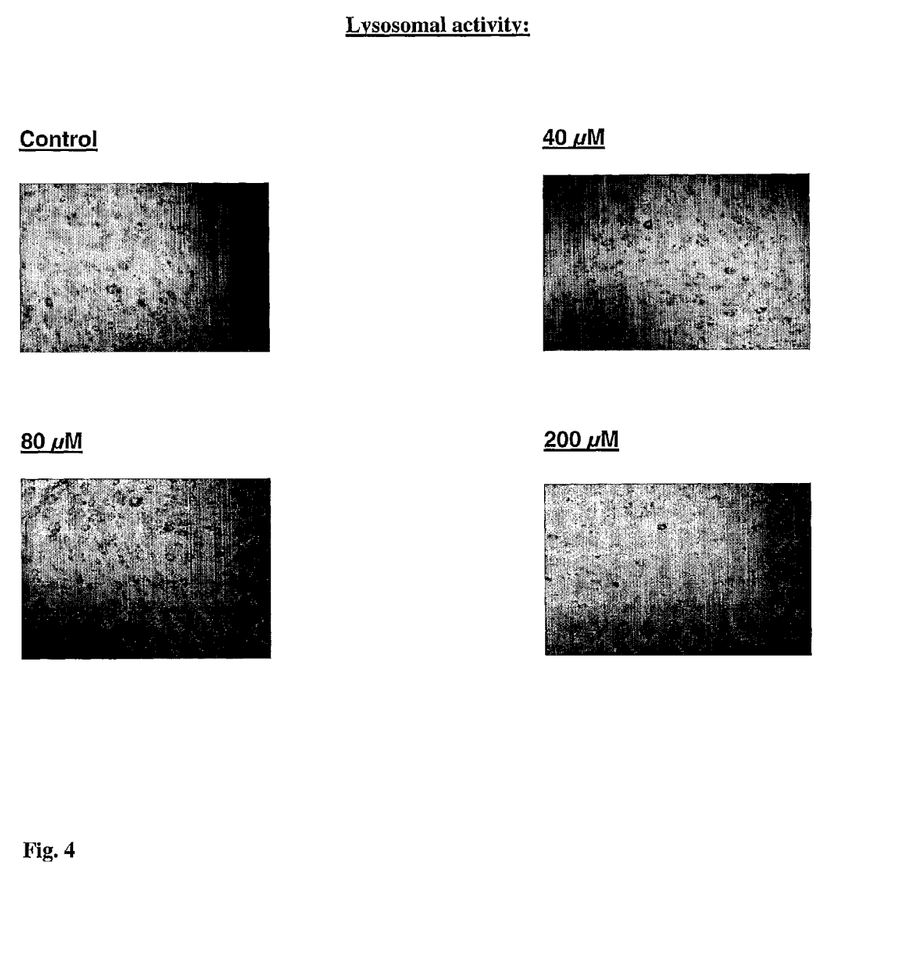
FIG. 4 presents the effect of phloretamide on SF25 p29 showing lysosomal staining (20×).

Staining for JC-1 was performed after phloretamide pre-treatment on dermal fibroblasts for a period of 3 days to see the mitochondrial potential. The population of cells shown in the FIG. 4 show polarized mitochondria from living cells marked by punctate orange-red fluorescent staining by the formation and maintenance of J-aggregates. Punctate orange-red fluorescent staining was observed within the 3-p-hydroxyphenyl-propionic acid amide treatment of cells at all doses.

Figure 11:
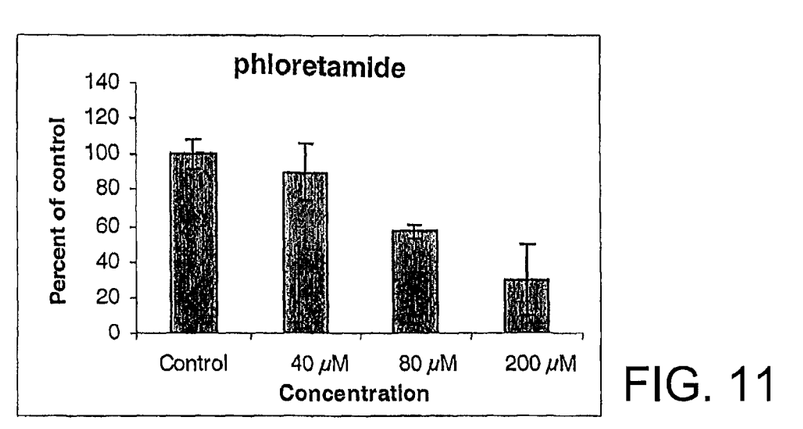

Effect of 3-p-hydroxyphenyl-propionic acid amide on lysosomal activity rate—The NRU (neutral red uptake) assay facilitates the rapid evaluation of the cytotoxicity of different screening compounds. Images in FIG. 4 suggest that the staining pattern of the cells showed autophagy (40 µM and 80 µM), and data from graph in FIG. 11 shows that up to 200 µM, the lysosomal rate of 3-p-hydroxyphenyl-propionic acid amide treated cells decreased in a dose dependent manner compared to the untreated.

At a dose range of 40 µM and 80 µM, results showed a 15-40% decrease in the lysosomal autophagy. In conclusion, a decrease in lysosomal activity was observed in cells treated with upwards of 40 µM phloretamide.

Figure 12:
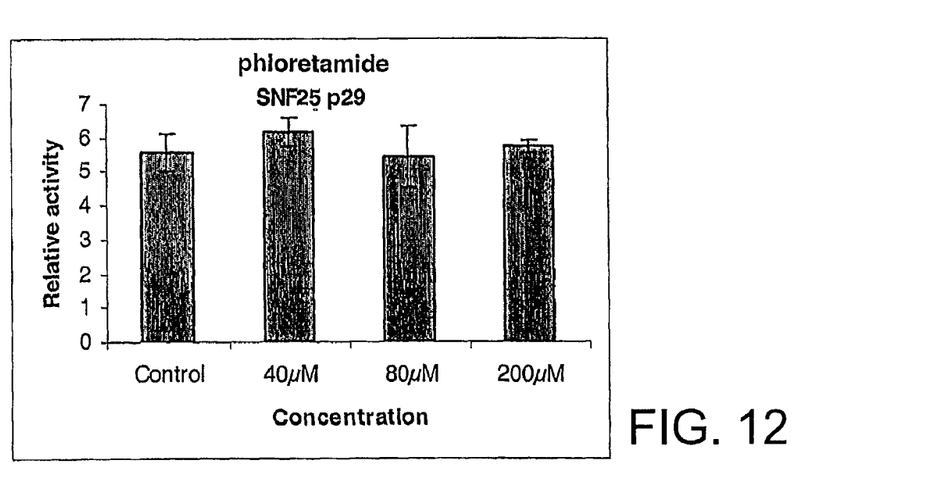

Effect of 3-p-hydroxyphenyl-propionic acid amide on chymotrypsin-like activity—As shown in FIG. 12, Phloretamide treatment (40 to 200 µM) showed no effect on the proteasomal activity of human cells.

Effects on late passage cells—Cytoskeletal organization: Late passage cells with more than 75% lifespan were treated with different doses of phloretamide in order to see if this treatment could revert any of the age related changes. The actin staining pattern in middle-aged cells after 3 days showed no obvious differences between treated and untreated cells.

Figure 5:
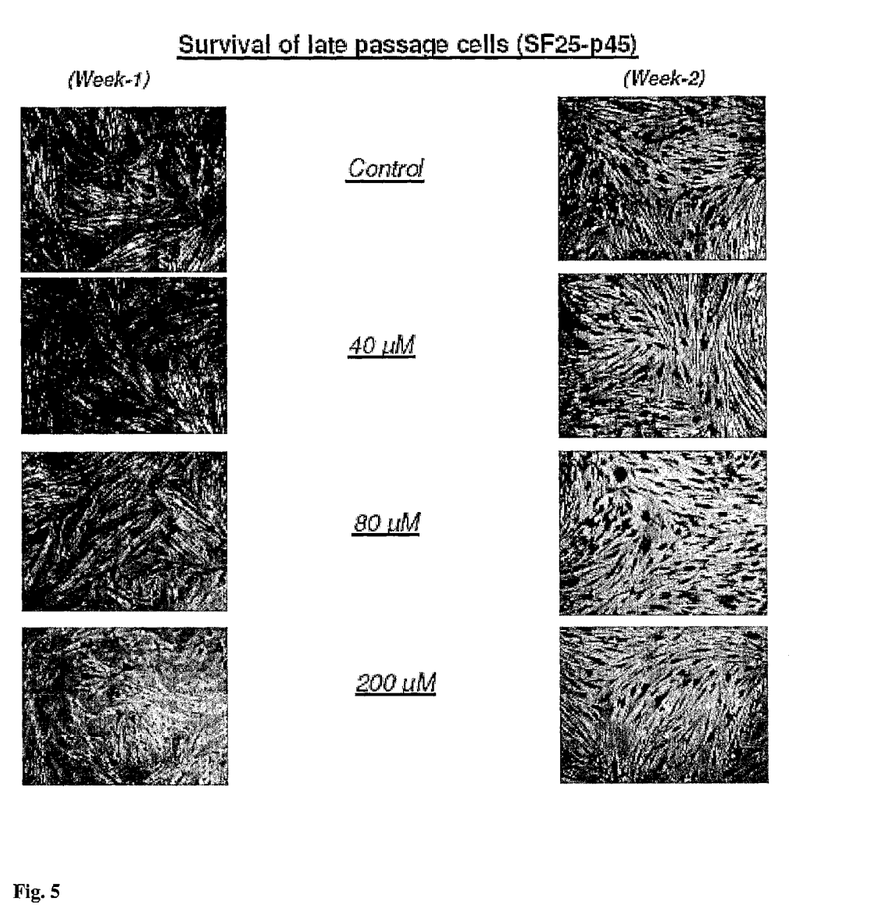
FIG. 5 presents the effect of phloretamide on the morphology of late passage cells after 7 and 14 days.

Effect of 3-p-hydroxyphenyl-propionic acid amide on the morphology of late passage cells after 7 and 14 days—Morphology of senescent cells: Late passage human skin fibroblasts (about 75% life span completed) were treated with various doses of phloretamide to see whether this treatment could reverse age-related alterations in their morphology. FIG. 5 shows that there were subtle differences in the appearance of cells after seven and fourteen days of treatment. Heterogeneous behavior was not observed in the cells. We couldn't find an improvement in the cells after 14 days of treatment.

Cell survival: Equal numbers of senescent cells were seeded in separate flasks and were treated with different concentrations of phloretamide. Cell numbers were determined by using a Coulter counter after trypsinization and resuspension of cells after 7 and 14 days of treatment.

Figure 13:
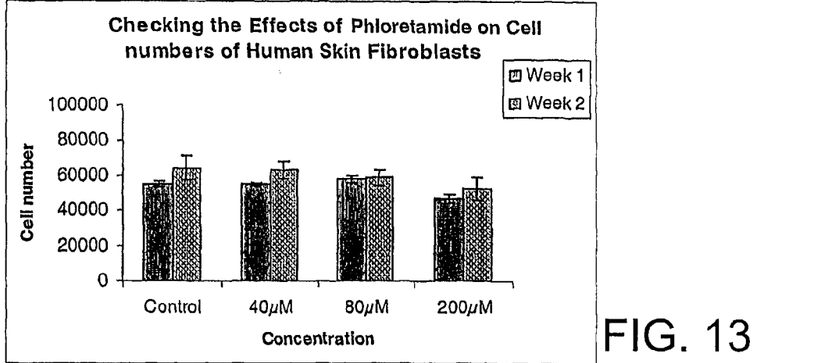

Number of cells after 7 days and 14 days of 3-p-hydroxyphenyl-propionic acid amide treatment—FIG. 13 shows that the numbers of surviving late passage cells after 3p-hydroxyphenyl-propionic acid amide treatment were almost similar without much difference after one and two weeks. However, at higher doses a dose dependent reduction in the cell growth was observed after 7 and 14 of treatment.

Induction of cell proliferation (DNA synthesis)—In order to ascertain whether phloretamide induced additional cell proliferation, we examined the extent of DNA synthesis.

Figure 14:
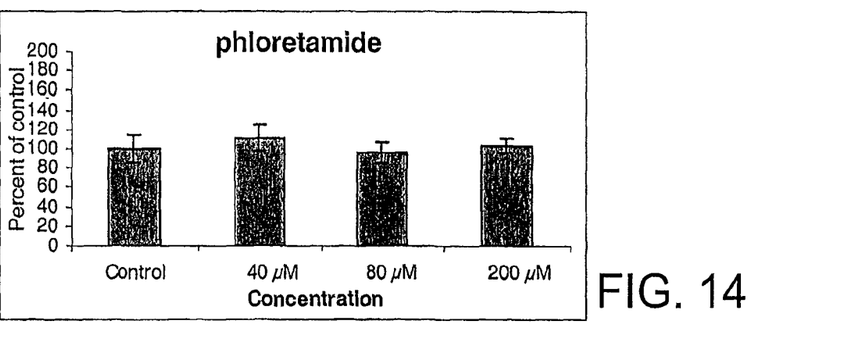

As shown in FIG. 14., our results showed that there were no significant differences in DNA synthesis in 3-phydroxyphenyl-propionic acid amide pre-treated fibroblasts in comparison to the controls.

Figure 6:
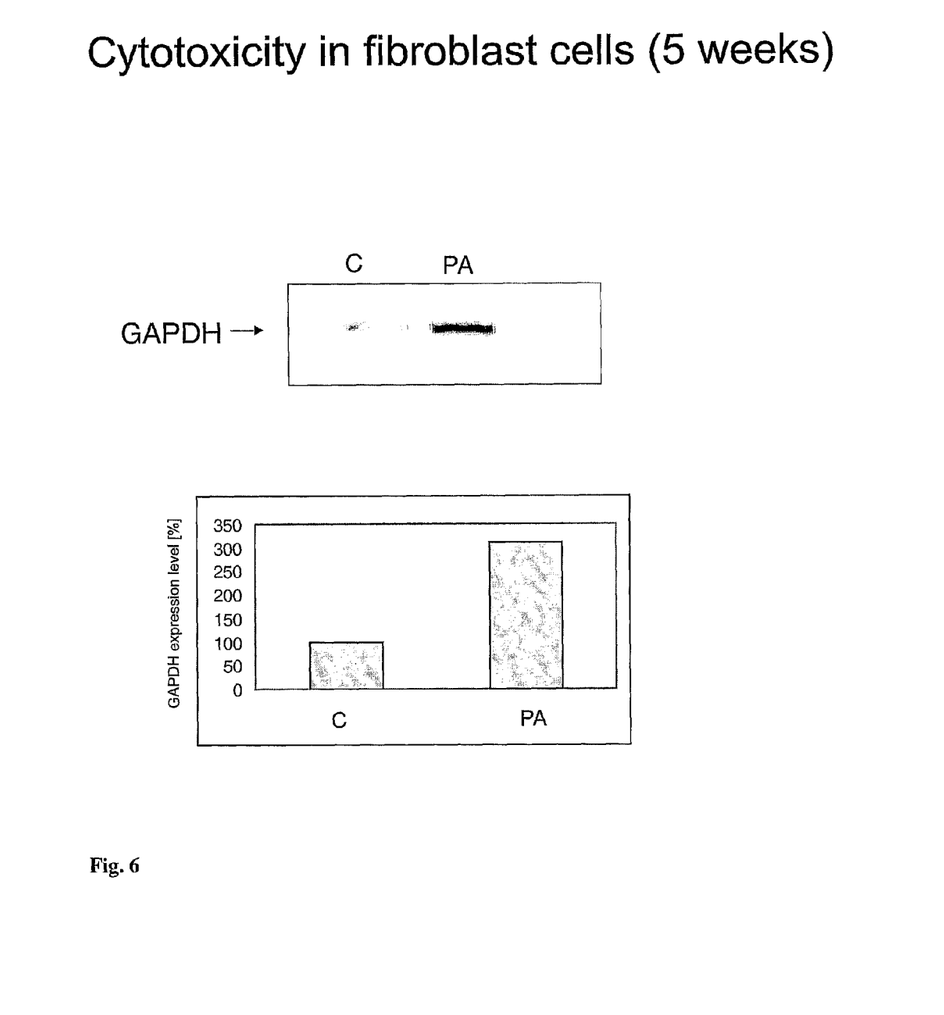
FIG. 6 presents an analysis of the level of expression of the GAPDH gene in fibroblasts treated with phloretamide following 5 weeks of treatment.

RT-PCR was performed on RNA isolated from line 1 cells (not treated with phloretamide) and line 2 cells (treated with 100 µM phloretamide). Differences in the expression of the GAPDH gene were determined using a Phosphorimager, and the ImageQant software. Data presented in FIG. 6.

Figure 7:
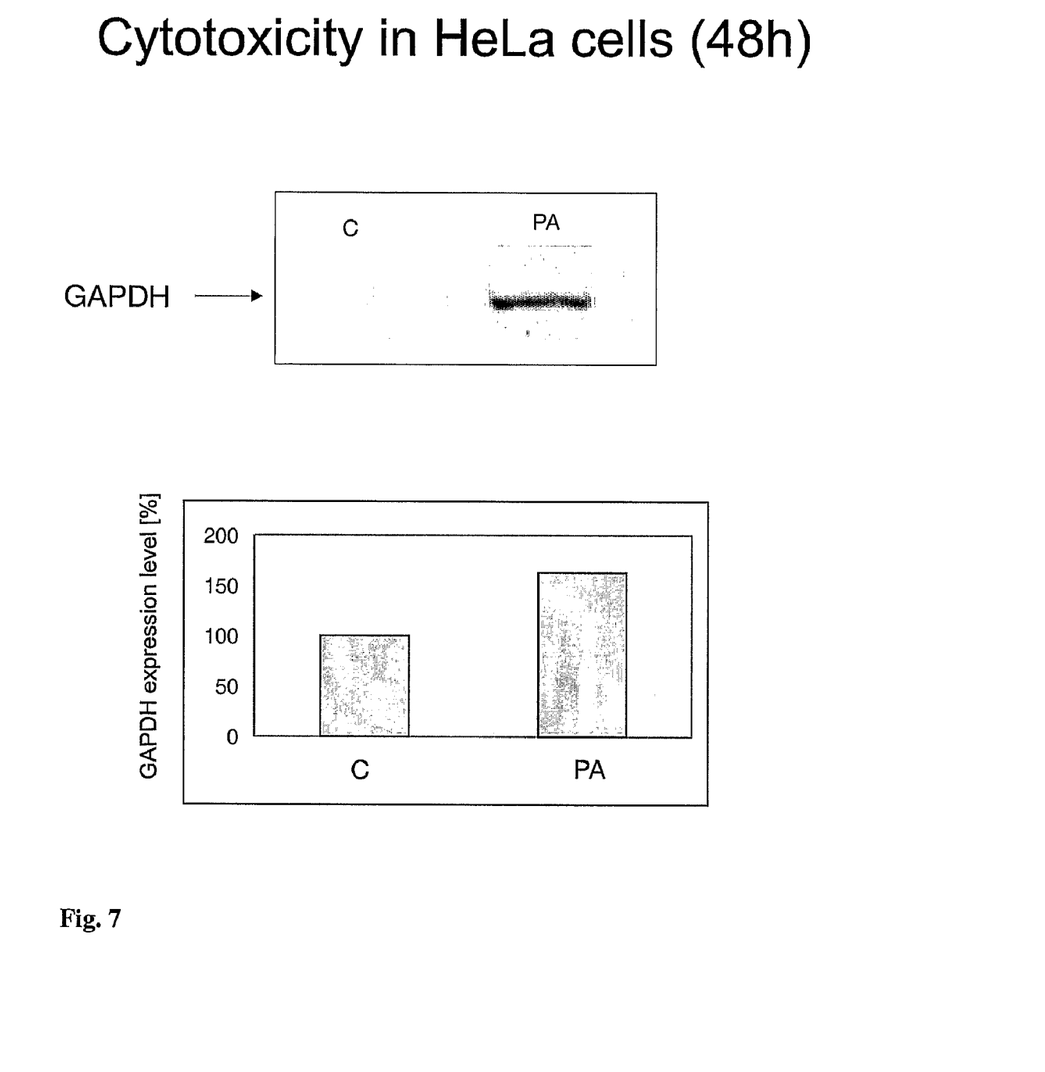
FIG. 7 represents an analysis of the level of expression of the GAPDH gene in HeLa cells treated with phloretamide after 48 hours of culture.

RT-PCR was performed on RNA isolated from line 1 cells (not treated with phloretamide) and line 2 cells (treated with 100 μM phloretamide). Differences in the expression of the GAPDH gene were determined using a Phosphorimager, and the ImageQant software. Data presented in FIG. 7.

Conclusions—The results obtained from this series of experiments on the short-term effects of phloretamide on human skin fibroblasts indicate that this compound has significant beneficial anti-aging effects and long term studies on dermal fibroblasts can be carried out. At 40 and 80 μM, enhanced cell attachment (10-20%) along with a stimulation of cell growth at 40 μM and 80 μM can be observed through a one step growth curve analysis (up to 11 days).

The invention claimed is:

1. A method of manufacturing 3-(4-hydroxyphenyl) propanoic acid amide using an active 4-nitrophenyl ester comprising:
   (a) reacting a mixture of 3-(4-hydroxyphenyl) propanoic acid with 4-nitrophenol in ethyl acetate supplemented with N,N'-dicyclohexylcarbodiimide;
   (b) stirring and reacting said reaction mixture in (a) to form a precipitate of N,N'-dicyclohexylurea;
   (c) filtering said precipitate;
   (d) drying said precipitate under vacuum;
   (e) adding anhydrous methanol saturated with ammonia to said dried precipitate;
   (f) stirring said precipitate mixed with anhydrous methanol saturated with ammonia;
   (g) evaporating said precipitate mixed with anhydrous methanol saturated with ammonia until dry to create a dried product;
   (h) loading said dried product onto a chromatography column packed with silica gel and washing with a chloroform-methanol mixture to create a chromatographically clean product;
   (i) crystallizing said chromatographically clean product from methanol; and
   (j) drying said chromatographically clean product in a vacuum dessicator to yield 3-(4-hydroxyphenyl) propanoic acid amide.

2. The method of claim 1 wherein in step (b) said reaction mixture is mixed and reacted in a temperature range of from 0° C. to 10° C. for from 10 to 50 minutes, then mixed at room temperature for from 1.5 to 3.0 hours.

3. The method of claim 1, wherein the reaction is represented by the following formula:

4. The method of claim 2, wherein the amount of N,N'-dicyclohexylcarbodiimide used is from 5 to 15 times excess of N,N'-dicyclohexylcarbodiimide in relation to the amount of 4-nitrophenyl used.

5. The method of claim 1, wherein in step (j) said chromatographyically clean product is dried in a vacuum dessicator over phosphorus pentoxide.

6. A method of manufacturing 3-(4-hydroxyphenyl) propanoic acid amide using an active 4-nitrophenyl ester comprising:
   (a) reacting a mixture of 3-(4-hydroxyphenyl) propanoic acid with 4-nitrophenol in ethyl oxide supplemented with N,N'-dicyclohexylcarbodiimide, wherein from 5 to 15 times excess of N,N'-dicyclohexylcarbodiimide in relation to 4-nitrophenol is used;
   (b) stirring and reacting said reaction mixture for from 10 to 50 minutes at a temperature of from 0° C. to 10° C. followed by stifling and reacting said reaction mixture for from 1.5 to 3.0 hours at room temperatures, to form a precipitate of N,N'-dicyclohexylurea;
   (c) filtering said precipitate;
   (d) washing said precipitate in ethyl acetate;
   (e) drying said precipitate under vacuum;
   (f) adding anhydrous methanol saturated with ammonia to said dried precipitate;
   (g) stirring said precipitate mixed with anhydrous methanol saturated with ammonia;
   (h) evaporating said precipitate mixed with anhydrous methanol saturated with ammonia until dry to create a dried product;
   (i) loading said dried product onto a chromatography column packed with silica gel and washing with a chloroform-methanol mixture to create a chromatographically clean product;
   (j) crystallizing said chromatographically clean product from methanol; and
   (k) drying said chromatographically clean product in a vacuum dessicator to yield 3-(4-hydroxyphenyl) propanoic acid amide.

7. The method of claim 6, wherein in step (k) said chromatographically clean product is dried in a vacuum dessicator over phosphorus pentoxide.

8. A cosmetic or pharmaceutical composition comprising 3-(4-hydroxyphenyl) propanoic acid amide.

9. The composition of claim 8, wherein said 3-(4-hydroxyphenyl) propanoic acid amide is present at a concentration of from 1 to 500 μM.

10. The composition of claim 9, wherein said 3-(4-hydroxyphenyl) propanoic acid amide is present at a concentration of from 40 to 200 μM.

11. The composition of claim 9, wherein said 3-(4-hydroxyphenyl) propanoic acid amide is made by the process comprising:
- (a) reacting a mixture of 3-(4-hydroxyphenyl) propanoic acid with 4-nitrophenol in ethyl acetate supplemented with N,N'-dicyclohexylcarbodiimide;
- (b) stirring and reacting said reaction mixture in (a) to form a precipitate of N,N'-dicyclohexylurea;
- (c) filtering said precipitate;
- (d) drying said precipitate under vacuum;
- (e) adding anhydrous methanol saturated with ammonia to said dried precipitate;
- (f) stirring said precipitate mixed with anhydrous methanol saturated with ammonia;
- (g) evaporating said precipitate mixed with anhydrous methanol saturated with ammonia until dry to create a dried product;
- (h) loading said dried product onto a chromatography column packed with silica gel and washing with a chloroform-methanol mixture to create a chromatographically clean product;
- (i) crystallizing said chromatographically clean product from methanol; and
- (j) drying said chromatographically clean product in a vacuum dessicator to yield 3-(4-hydroxyphenyl) propanoic acid amide.

12. The composition of claim 9, wherein said 3-(4-hydroxyphenyl) propanoic acid amide is made by the process comprising:
- (a) reacting a mixture of 3-(4-hydroxyphenyl) propanoic acid with 4-nitrophenol in ethyl oxide supplemented with N,N'-dicyclohexylcarbodiimide, wherein from 5 to 15 times excess of N,N'-dicyclohexylcarbodiimide in relation to 4-nitrophenol is used;
- (b) stirring and reacting said reaction mixture for from 10 to 50 minutes at a temperature of from 0° C. to 10° C. followed by stifling and reacting said reaction mixture for from 1.5 to 3.0 hours at room temperatures, to form a precipitate of N,N'-dicyclohexylurea;
- (c) filtering said precipitate;
- (d) washing said precipitate in ethyl acetate;
- (e) drying said precipitate under vacuum;
- (f) adding anhydrous methanol saturated with ammonia to said dried precipitate;
- (g) stirring said precipitate mixed with anhydrous methanol saturated with ammonia;
- (h) evaporating said precipitate mixed with anhydrous methanol saturated with ammonia until dry to create a dried product;
- (i) loading said dried product onto a chromatography column packed with silica gel and washing with a chloroform-methanol mixture to create a chromatographically clean product;
- (j) crystallizing said chromatographically clean product from methanol; and
- (k) drying said chromatographically clean product in a vacuum dessicator to yield 3-(4-hydroxyphenyl) propanoic acid amide.

* * * * *